US006521254B2

(12) United States Patent
Weinstein et al.

(10) Patent No.: US 6,521,254 B2
(45) Date of Patent: *Feb. 18, 2003

(54) SINGLE-DOSE ANTIHISTAMINE/ DECONGESTANT FORMULATIONS FOR TREATING RHINITIS

(75) Inventors: Robert E. Weinstein, Boston, MA (US); Allan M. Weinstein, Potomac, MD (US)

(73) Assignee: J-Med Pharmaceuticals, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/757,852

(22) Filed: Jan. 10, 2001

(65) Prior Publication Data

US 2001/0011102 A1 Aug. 2, 2001

Related U.S. Application Data

(63) Continuation-in-part of application No. 09/550,761, filed on Apr. 17, 2000, which is a continuation-in-part of application No. 09/206,713, filed on Dec. 7, 1998, now Pat. No. 6,051,585.

(51) Int. Cl.[7] .............................. A61K 9/22; A61K 9/20
(52) U.S. Cl. ....................... 424/468; 424/400; 424/439; 424/465; 424/466; 424/464; 424/488; 424/489; 514/159; 514/224; 514/335; 514/290
(58) Field of Search ................................ 424/439, 465, 424/466, 468, 489, 488; 514/159, 224, 335, 290

(56) References Cited

U.S. PATENT DOCUMENTS

| 4,975,426 A | * | 12/1990 | Sunshine et al. ............ 514/159 |
| 5,314,697 A | | 5/1994 | Kwan et al. ................. 242/480 |
| 5,869,479 A | * | 2/1999 | Kreutner et al. ....... 514/217.05 |
| 6,051,585 A | * | 4/2000 | Weinstein et al. .......... 514/335 |

FOREIGN PATENT DOCUMENTS

| EP | 0 396 404 | 11/1990 | .......... A61K/31/445 |
| WO | WO98/18470 | 5/1998 | .......... A61K/31/445 |

OTHER PUBLICATIONS

Bronsky, E. M.D., et al., "Comparative Efficacy and Safety of a Once–Daily Loratadine–Pseudoephedrine Combination Versus its Components alone and placebo in the Management of Seasonal Allergic Rhinitis" *J. Allergy and Clin. Immunol.*, 69, pp. 139–147 (1995).
Kosoglou, T. Ph.D. et al., "Pharmacokinetics of Loratadine and Pseudoephedrine Following Single and Multiple Doses of Once–Versus Twice–Daily Combination Tablet Formulations in Healthy Adult Males" *Clinical Therapeutics*, 19, pp. 1002–1012 (1997).

Horak, F. et al., "Efficacy and Tolerability of Astemizole–D and Loratadine–D During Prolonged, Controlled Allergen Challenge in the Vienna Challenge Chamber" *Arzneim–Forsch./Drug Res.*, 46, p. 1077–1081 (1996).
Rombaut et al., "Effects of Oral Administration of Different Formulations of Pseudoephedrine on Day–and Night–Time CNS Activity" *Med. Sci. Res.*, 17, pp. 831–833 (1989).
Negrini, A.C. et al., Oral Antihistamine/Decongestant Treatment Compared with Intranasal Corticosteroids in Seasonal Allergic Rhinitis *Clinical & Exp. Allergy*, 25, pp. 60–65 (1995).
Empey, D.W. et al., "Dose–Response Study of the Nasal Decongestant and Cardiovascular Effects of Pseudoephedrine" *Br. J. Clin. Pharmac.*, 9, pp. 351–358 (1980).
Idzikowski C. et al. "The Effect of Astemizole, Terfenadine and Psuedoephedrine Combinations of Sleep in Healthy Volunteers" *Allergy*, 87, (Suppl) 100 (1992).
Janssens M.M. and L Caers L.I, "Onset of Action of Astemizole" *Int. J. Clin. Pharm. Res.*, 11, pp. 219–229 (1991).
Yacobi A., et al., "Evaluation of Sustained–Action Chlorpheniramine–Psudoephedrine Dosage Form in Humans" *J. Pharm. Sci.*, 69, pp. 1077–1081 (1980).
Nomeir, A. A. Ph.D., et al., "Influence of Food on the Oral Bioavailability of Loratadine and Pseudoephedrine from Extended36 –Release Tables in Healthy Volunteers" *J. Clin. Pharmacol.*, pp. 923–939 (1996).
Dickerson, J., et al., "Dose Tolerance and Pharmacokinetic Studies of L–(+) Pseudoephedrine Capsules in Man" *Europ. J. Clin. Pharmacol.*, 14, 253–59 (1978).
D'Ambrosio F. P., et al. "Astemizole–D Compared with Triprolidine–D (Actifed) for Acute Treatment of Perennial Allergic Rhinitis" *J. Pharm. Med.*, 4 pp. 15–22 (1994).
Kanfer, I. Ph.D. et al., "Pharmacokinetics of Oral Decongestants" *Pharmcotherapy*, 13, pp. 116S–28S.
Bye, C. et al., A Comparison of Plasma Levels of L(+) Pseudoephedrine Following Different Formulations, and Their Relation to Cardiovascular and Subjective Effects in Man *Eur. J. Clin. Pharmacol.*, 8, 47–53 (1975).

* cited by examiner

Primary Examiner—Thurman K. Page
Assistant Examiner—Charesse Evans
(74) Attorney, Agent, or Firm—Heslin Rothenberg Farley & Mesiti P.C.

(57) ABSTRACT

Pharmaceutical dosage forms for oral administration of an antihistamine and a decongestant are disclosed. The dosage forms provide an antihistamine in an amount and formulation to exhibit antihistaminic activity in a human for greater than 22 hours; and a decongestant in an amount and formulation to exhibit stimulatory activity in a human for less than 16 hours. The formulation of the invention can be taken once per day to afford symptomatic relief of rhinitis while avoiding stimulation at night.

23 Claims, No Drawings

SINGLE-DOSE ANTIHISTAMINE/ DECONGESTANT FORMULATIONS FOR TREATING RHINITIS

CROSS-REFERENCE TO RELATED APPLICATIONS

This application is a continuation-in-part of U.S. application Ser. No. 09/550,761, filed Apr. 17, 2000, which is a continuation-in-part of U.S. application Ser. No. 09/206,713, filed Dec. 7, 1998, now U.S. Pat. No. 6,051,585. The entire disclosures of both are incorporated herein by reference.

1. Field of the Invention

The present invention relates to pharmaceutical compositions, in particular oral dosage forms for rhinitis comprising a combination of decongestant and antihistamine.

2. Background

Rhinitis refers to an inflammatory disorder of the nasal passages. The symptoms of rhinitis typically consist of sneezing, rhinorrhea, nasal congestion, and increased nasal secretions. Failure of treatment of rhinitis may lead to other disorders that include infection of the sinuses, ears, and lower respiratory tract. Two types of oral medication are commonly used to treat the symptoms of rhinitis, decongestants and antihistamines. Decongestants and antihistamines differ in their mechanisms of action, therapeutic effects, and side effects. It is common practice to combine both of these medications to bring about more complete symptom relief of rhinitis than with either entity alone.

Decongestants commonly used to treat rhinitis include the adrenaline-like agents pseudoephedrine and phenylpropanolamine. These agents act to constrict vessels in the nasal mucus membranes and thereby decrease tissue swelling and nasal congestion. Decongestants are found to be better than antihistamines for restoring the patency of congested nasal airways. Like adrenaline, nasal decongestants are stimulatory and produce side effects that may be tolerated while the user is awake, and may even be considered desirable to counter fatigue that is known to accompany other symptoms of rhinitis. Decongestants, however, may produce nervousness, restlessness, and insomnia if taken when sleep is desired. This can be a source of confusion for individuals, who mistakenly attribute their inability to sleep to the malaise that may accompany other rhinitis symptoms, rather than to the decongestant medication.

Histamine is a mediator released from cells that line the walls of the nasal mucous membranes (mast cells). When released, histamine binds to local histamine receptors causing sneezing, nasal itching, swelling of the nasal membranes, and increased nasal secretions. Antihistamines relieve these effects, albeit by a different mechanism than decongestants. Antihistamines block the binding of histamines to the histamine receptors by preemptively binding to the receptors. Consequently they are effective only if given prior to histamine release since once histamine is released and binds to the receptors, it is too late. Although individuals typically take antihistamines after symptoms occur, it is more desirable to dose antihistamines so as to effect therapeutic availability in anticipation of histamine release. Antihistamines are generally sedating. However, newer antihistamines with no or little sedation have been developed in the last twenty years.

Combining decongestants and antihistamines utilizes both mechanistic approaches, and has been shown to offer more complete relief of rhinitis symptoms than therapy with either component alone. Consequently, many products have been formulated so that their dosage units contain both. The incorporation of decongestant and sedating antihistamine into a single dosage unit attempts a balance between the stimulating and sedating side effects of these components.

However, individuals are known to vary in their susceptibility to these side effects. Consequently, some individuals experience sedation when taking these combinations during the day or stimulation and insomnia when taking the combinations at night. More recently, formulations have been commercialized which incorporate a decongestant and a non-sedating antihistamine into a single dosage unit for the purpose of avoiding daytime sedation. Such combinations might be expected to provoke a greater incidence of nighttime irritability and insomnia because the stimulating side effects of decongestant are not attenuated by concomitant sedation by antihistamine. Indeed, a 25% incidence of insomnia has been disclosed among users of a commercialized combination of the non-sedating antihistamine terfenadine and the decongestant pseudoephedrine. Examples of such formulations include:

SELDANE-D® Extended-Release Tablets which contains 60 mg terfenadine (non-sedating antihistamine) and 120 mg pseudoephedrine hydrochloride (stimulating decongestant), and which is recommended to be taken every 12 hours (adults and children over 12 years of age).

ALLEGRA-D® contains 60 mg fexofenadine (non-sedating antihistamine) and 120 mg pseudoephedrine hydrochloride (stimulating decongestant), and which is recommended to be taken every 12 hours (adults and children over 12 years of age).

CLARITIN-D® 24-HOUR Extended-Release Tablets which contains 10 mg loratidine (non-sedating antihistamine) and 240 mg pseudoephedrine hydrochloride (stimulating decongestant), and which is recommended to be taken every 24 hours (adults and children over 12 years of age).

These and all currently marketed single entity combinations, which are formulated with decongestant and antihistamine, fail to address the problem of nighttime irritability and insomnia, a problem that is increased by combining non-sedating, rather than sedating antihistamine. Note is made of prior art which is directed toward reducing the side effects of antihistamines and decongestants. U.S. Pat. No. 4,295,567, issued to Knudsen, teaches a regimen for employing separate day and night dosage units for the purpose of avoiding daytime sedation from sedating antihistamines. This patent does not anticipate the advent of non-sedating antihistamine and overlooks the side effect of nighttime stimulation from decongestants. A regimen, commercialized as SYN-RX™, also employs separate day and night dosage units. SYN-RX™ contains a daytime formulation of 600 mg guaifenesin, which is non-stimulating, and 60 mg pseudoephedrine, which is stimulating, and a nighttime formulation of 600 mg of guaifenesin alone. SYN-RX™ does not contain an antihistamine. In failing to contain any medication that would be effective for the common symptoms of rhinitis at night, SYN-RX™ does not constitute a treatment for rhinitis. The use of multi-dosage unit regimens of such prior art is less convenient for a user than a single dose, once-per-day formulation, and more complex to follow, adding the potential for a user to confuse dosage units.

Individuals with rhinitis utilize antihistamines and decongestants together many of millions of times a year. Professional as well as consumer confusion is widely encountered with the use of these medications together, and unnecessarily negative consequences occur both by self-selection and prescription. In particular, individuals treated with decongestants at night not only risk insomnia, but also daytime irritability, fatigue, and malaise from lack of rest. It is known that these side effects are sometimes mistakenly ascribed to rhinitis rather than to the medication causing them. There is a present need for formulations which circumvent this confusion and which avoid nighttime stimulation.

SUMMARY OF THE INVENTION

It is an object of the present invention to simplify the combined use of antihistamine and nasal decongestant medications to enhance convenience, reduce patient errors and minimize side effects of the combined medications. The formulation of the invention can be taken once per day and avoids stimulation at night.

In one aspect the invention relates to oral dosage units comprising: (a) an antihistamine in an amount and formulation to exhibit antihistaminic activity in a human for greater than 22 hours; and (b) a decongestant in an amount and formulation to exhibit stimulatory activity in a human for less than 16 hours. The decongestant amount and formulation may also exhibit decongestant activity in a human for less than 16 hours.

In a closely related aspect, the invention relates to oral dosage units in which the decongestant is formulated to release decongestant non-linearly, such that discontinuity of release occurs between 12 and 16 hours and some portion of decongestant is released beyond 12 hours. To the extent that decongesting activity can be separated from stimulatory activity by control of serum concentration of the decongestant, it may be advantageous to maintain a lower, but decongestively effective serum concentration beyond 12 hours.

As noted, individuals are known to vary in their susceptibility to the stimulating side effects of decongestants, and it is an important object of the present invention to provide a formulation in which such stimulation is minimized or absent in the 16–24 hour period after dosing in most individuals, in contrast to the stimulatory activity found to interfere with sleep in 25% of individuals taking present decongestant-non-sedating antihistamine formulations.

In another aspect, the invention relates to a method of providing treatment for rhinitis in a human comprising: (a) formulating an amount of an antihistamine to exhibit antihistaminic activity in a human for greater than 22 hours; (b) formulating an amount of a decongestant to exhibit stimulatory activity in a human for less than 16 hours; (c) combining the antihistamine and the decongestant in a single oral dosage unit; and (d) providing instructions to administer the oral dosage unit at the start of the day.

In another aspect, the invention relates to a kit, which provides a once-per-day dosage regimen for treating rhinitis, while avoiding stimulation at night. The kit comprises: (a) an oral dosage form containing an amount of an antihistamine to exhibit antihistaminic activity in a human for greater than 22 hours; (b) an oral dosage form containing an amount of a decongestant to exhibit stimulatory activity in a human for less than 16 hours; and (c) instructions to administer the antihistamine and decongestant at the start of the day. The antihistamine and the decongestant may be in separate dosage units or may be combined in a single oral dosage unit.

The single dosage unit of the present invention for treating the symptoms of rhinitis may additionally include other medications, such as an analgesic.

DETAILED DESCRIPTION OF THE INVENTION

The single dosage unit of the present invention for treating the symptoms of rhinitis contains a combination of medications that include nasal decongestants and antihistamines. The dosage unit may be in the form of a tablet, pill, capsule, caplet, or other recognized oral form of medication. The dosage unit contains a sedating or non-sedating antihistamine, and the components are formulated so as to produce the pharmacokinetic and therapeutic characteristics desired. The preparation such formulations employs techniques well-known in the art.

Preferred decongestants are pseudoephedrine and phenylpropanolamine. To achieve the desired release profile, the pseudoephedrine is usually present in an amount of 120 mg or less for embodiments that exhibit stimulatory and/or decongesting activity in a human for less than 16 hours. When decongesting activity beyond 16 hours is desired, an amount of 120 mg to 160 mg of pseudoephedrine is formulated for non-linear release, so that up to 120 mg is released within 12 hours of administration, a discontinuity of release occurs between 12 and 16 hours and the remainder is released after the discontinuity, i.e. beyond 12 hours. To achieve the desired release profile, the phenylpropanolamine is usually present in an amount of 75 mg or less for embodiments that exhibit stimulatory and/or decongesting activity in a human for less than 16 hours. When decongesting activity beyond 16 hours is desired, an amount of 75 mg to 100 mg of phenylpropanolamine is formulated for non-linear release, so that up to 75 mg is released within 12 hours of administration, a discontinuity of release occurs between 12 and 16 hours and the remainder is released after the discontinuity. Oral sustained release drug delivery systems are well known to those skilled in the art, and general methods of achieving sustained release of orally administered drugs are found in any standard pharmacy school textbook, for example *Remington: The Science and Practice of Pharmacy*. Chapter 94 of the 19th edition of Remington entitled "Sustained-Release Drug Delivery Systems" describes the more common types of oral sustained-release dosage forms (pages 1660–1675.) The disclosure is incorporated herein by reference. To obtain a discontinuity of release, when that is desired, one would normally formulate a portion of the decongestant in a sustained-release formulation and another portion in a delayed-release formulation. For example, one may prepare one set of granules of pseudoephedrine for immediate release, another set of granules of pseudoephedrine with hardened gelatin, methyl or ethyl cellulose, polyhydroxymethacrylate, or hydroxypropylcellulose for sustained release and, when a lower serum concentration beyond 12 hours is desired, a third set of granules of pseudoephedrine coated with an acrylic resin, such as an EUDRAGIT™ resin, for delayed release. The various types of pseudoephedrine granules are then mixed in appropriate proportion for the desired release profile and filled into gelatin capsules with the antihistamine.

Preferred antihistamines include loratidine, descarboethoxyloratidine, cetirizine, astemizole, norastemizole and fexofenadine. The loratidine, astemizole and norastemizole are preferably in an amount of 10 mg or more. The cetirizine and descarboethoxyloratidine are preferably in an amount of 5 mg or more. The fexofenadine is preferably in an amount of 120 mg or more.

The duration of antihistaminic activity of a particular formulation in a human may be measured most readily by the well-known wheal-and-flare test, but the use of a "Vienna Challenge Chamber" as described by Hayrack et al. [*Arzneim.-Forsch.* 46, 1077–1081 (1996); *Klin. Wochenschr.* 14, 509 (1987) and *J. Int. Med. Res.* 20, 422 (1992)] provides a measure that is presumably closer to the clinical situation for rhinitis. In the United States, the Food and Drug Administration (FDA) must approve a drug for the therapeutic efficacy and safety before it can be marketed, and approve the labeling for its recommended dosing. Antihistamines which have met the FDA standard of having a duration of therapeutic benefit suitable for 24 hour dosing and which are so labeled are: cetirizine 5 mg; cetirizine 10 mg; loratidine 10 mg; and fexofenadine 180 mg. The duration of decongestant activity can be measured as described by Empey et al. *Br. J. Clin. Pharmacol.* 9, 351–358 (1980) for nasal airway resistance. The duration of stimulatory activity of the decongestant may be evaluated by observing pulse rate elevation [also described by Empey et al. *Br. J. clin. Pharmacol.* 9, 351–358 (1980) and by Dickerson et al. *Europ. J. clin. Pharmacol.* 14, 253–259 (1978)] or by observing EEG activity as described by Rombaut et al. *Med. Sci. Res.* 17, 831–833 (1989). The disclosures of these references are incorporated herein by reference.

The terms "day" and "night" as used herein are intended to be synonymous with the period of wakefulness, when stimulation might be acceptable, and the period of sleeping, when stimulation would be undesired, respectively. Such times vary in accordance with the schedule of individuals.

Examples of the single dosage units of the present invention include:

EXAMPLE 1

A single dosage unit consisting of 120 mg pseudoephedrine, a stimulating decongestant, prepared so as to be released over a 10–12 hour time, and 10 mg loratidine, a non-sedating antihistamine, formulated so as to be released immediately. When taken at the start of the day (a time anticipating a desire to be awake for 12 to 16 hours), this dosage unit provides immediate dosing with loratidine, which is known to exert an antihistaminic effect 1 to 3 hours after dosing, reach a maximum at 8 to 12 hours, and last in excess of 24 hours. Once released, pseudoephedrine has a 4 to 6 hour half-life, considerably shorter than that of loratidine. The comparatively short decongestant effect of pseudoephedrine is extended by a sustained release formulation. This dosage unit provides both immediate and delayed action of pseudoephedrine, so as to exert a decongestant effect during waking hours, when the stimulation of pseudoephedrine is best tolerated, but not at night. One such time-release method, well-known in the art, involves formulation of the decongestant with cellulose ether base materials, such as hydroxypropyl methylcellulose. Such time-release methods may be utilized to delay the bioavailability of all or only a portion of the ingested dose, and for varying lengths of time. The antihistamine and decongestant components of this formulation are similar to that of CLARITIN-D® 24-HOUR Extended-Release Tablets which contain 10 mg loratidine (antihistamine) and 240 mg pseudoephedrine hydrochloride (decongestant), and which are recommended to be taken every 24 hours in adults. The present invention formulation differs, however, in that it contains a lesser dose of pseudoephedrine, and that it limits the duration of action of pseudoephedrine to 12–16 hours, thus avoiding the stimulation of pseudoephedrine at night.

EXAMPLE 2

A single dosage unit consisting of 75 mg phenylpropanolamine, a stimulating decongestant, prepared so as to be released over a 10-hour time period, and 10 mg cetirizine, a non-sedating antihistamine, prepared so as to be released immediately. When taken at the start of the day, this formulation provides immediate dosing with cetirizine, which is known to exert an antihistaminic effect within one hour after dosing and to persist for 24 hours. This formulation also preferably provides immediate and delayed action of phenylpropanolamine over a period not to exceed 16 hours after administration so as to exert effect during daytime hours, when stimulation is best tolerated, but exerts no effect at night. Like pseudoephedrine, the comparatively short half-life and decongestant effect of phenylpropanolamine are prolonged in this formulation by incorporating a prolonged release of phenylpropanolamine over time so as to achieve efficacy through the waking hours, but not so long as to provide phenylpropanolamine activity during the time when stimulation is undesired.

EXAMPLE 3

A single dosage unit consisting of 75 mg pseudoephedrine, a stimulating decongestant prepared so as to be released over a 10-hour time period, and 120 mg of fexofenadine, a non-sedating antihistamine, formulated so as to be active over a 24-hour period. Fexofenadine, when given alone, exhibits antihistaminic effect within one hour, achieves a maximum effect at 12 hours, and still has a measurable effect at 24 hours. This formulation provides immediate and delayed activity of fexofenadine over a 24-hour span and of pseudoephedrine over a period not in excess of 16 hours after administration.

EXAMPLE 4

A once-per-morning dosage, in syrup form, consisting of 5 mg cetirizine (immediate release), and 30 mg of pseudoephedrine (immediate release). This dosage contains a quantity of cetirizine which provides a therapeutic antihistaminic therapeutic benefit for 24 hours. The pseudoephedrine, immediately released, results in a 4–6 hour duration of action during the early part of the day. The formulation would be particularly appropriate for children from ages 6–11, as it is in liquid form, and it has decongestant action early in the day, during school hours. This timing would accomplish decongestant action at a time when symptoms often peak, and when such action is needed. It is noted that cetirizine is associated with slightly more sedation than other non-sedating antihistamines but not as great as sedating antihistamines. In those individuals who experience sedation with cetirizine, the simulation of decongestant, during initial absorption, when blood levels of cetirizine peak, might be desirable. This dosage would not cause stimulation later in the day at more sedentary times or interfere with sleep at night. Individuals differ in their susceptibility to the stimulatory side effects of decongestants, and this dosage regimen might also be particularly suitable for an adult individual who is sensitive to decongestant side effects, but who can tolerate a short period of stimulation early in the day.

In addition to antihistamines and decongestants, additional therapeutic ingredients for the treatment of rhinitis may be formulated if desired. For example, leukotriene inhibitors and analgesics such as salicylates and acetaminophen may be considered for inclusion in such dosage units and are within the scope of this invention. These examples do not constitute an exhaustive list of potential combinations, and variations and modifications may be made by those of ordinary skill in the art. Those of skill in the art may also recognize modifications to these presently disclosed embodiments. One such modification might involve a time-release of decongestant over periods other than those exemplified, but not so as to allow stimulation at night. These variations and modifications are meant to be covered by the spirit and scope of the present claims.

We claim:

1. An oral dosage unit consisting essentially of:
   (a) an antihistamine in an amount and formulation to exhibit antihistaminic activity in a human for greater than 22 hours; and
   (b) a decongestant in an amount and formulation to exhibit stimulatory activity in a human for less than 16 hours.

2. An oral dosage unit according to claim 1 wherein said decongestant is in an amount and formulation to exhibit decongestant activity in a human for less than 16 hours.

3. An oral dosage unit according to claim 1 wherein said decongestant is formulated to release said decongestant non-linearly such that discontinuity of release occurs between 12 and 16 hours and some portion of decongestant is released beyond 12 hours.

4. An oral dosage unit according to claim 1 or 2 wherein said decongestant is pseudoephedrine.

5. An oral dosage unit according to claim 4 wherein said pseudoephedrine is present in an amount of 120 mg or less.

6. An oral dosage unit according to claim 3 wherein said decongestant is pseudoephedrine.

7. An oral dosage unit according to claim 6 wherein said pseudoephedrine is present in an amount of 120 mg to 160 mg, formulated so that up to 120 mg is released within 12 hours of administration.

8. An oral dosage unit according to claim 1 or 2 wherein said decongestant is phenylpropanolamine.

9. An oral dosage unit according to claim 8 wherein said phenylpropanolamine is present in an amount of 75 mg or less.

10. An oral dosage unit according to claim 3 wherein said decongestant is phenylpropanolamine.

11. An oral dosage unit according to claim 10 wherein said phenylpropanolamine is present in an amount of 75 mg to 100 mg, formulated so that up to 75 mg is released within 12 hours of administration.

12. An oral dosage unit according to claim 1, 2 or 3 wherein said antihistamine is loratidine, descarboethoxyloratidine or cetirizine.

13. An oral dosage unit according to claim 12 wherein said loratidine is present in an amount of 10 mg or more.

14. An oral dosage unit according to claim 12 wherein said descarboethoxyloratidine or cetirizine is present in an amount of 5 mg or more.

15. An oral dosage unit according to claim 1, 2 or 3 wherein said antihistamine is astemizole.

16. An oral dosage unit according to claim 15 wherein said astemizole is present in an amount of 10 mg or more.

17. An oral dosage unit according to claim 1, 2 or 3 wherein said antihistamine is norastemizole.

18. An oral dosage unit according to claim 17 wherein said norastemizole is present in an amount of 10 mg or more.

19. An oral dosage unit according to claim 1, 2 or 3 wherein said antihistamine is fexofenadine.

20. An oral dosage unit according to claim 19 wherein said fexofenadine is present in an amount of 120 mg or more.

21. A kit for treating rhinitis in a human comprising:
    (a) an oral dosage form containing an amount of an antihistamine to exhibit antihistaminic activity in a human for greater than 22 hours;
    (b) an oral dosage form containing an amount of a decongestant to exhibit stimulatory activity in a human for less than 16 hours; and
    (c) instructions to administer the antihistamine and decongestant at the start of the day.

22. A kit according to claim 21 wherein the antihistamine and the decongestant are combined in a single oral dosage unit.

23. A method of providing treatment for rhinitis in a human comprising:
    (a) formulating an amount of an antihistamine to exhibit antihistaminic activity in a human for greater than 22 hours;
    (b) formulating an amount of a decongestant to exhibit stimulatory activity in a human for less than 16 hours;
    (c) combining the antihistamine and the decongestant in a single oral dosage unit consisting essentially of antihistamine and decongestant; and
    (d) providing instructions to administer the oral dosage unit at the start of the day.

* * * * *